US00PP37595P2

(12) United States Plant Patent
Weber

(10) Patent No.: US PP37,595 P2
(45) Date of Patent: Aug. 18, 2026

(54) RASPBERRY PLANT NAMED 'Crimson Beauty'

(50) Latin Name: ***Rubus idaeus* L**
Varietal Denomination: Crimson Beauty

(71) Applicant: Cornell University, Ithaca, NY (US)

(72) Inventor: Courtney Weber, Geneva, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 19/327,950

(22) Filed: Sep. 12, 2025

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./204
See application file for complete search history.

(56) References Cited

U.S. PATENT DOCUMENTS

PP10,412 P 5/1998 Swartz et al.
PP32,799 P2 2/2021 Weber

*Primary Examiner* — Susan McCormick Ewoldt
(74) *Attorney, Agent, or Firm* — Foley & Lardner LLP

(57) ABSTRACT

This invention relates to a new and distinct primocane bearing red raspberry plant designated as 'Crimson Beauty' primarily adapted to growing conditions of west central New York and other regions of similar climate. The new plant is primarily characterized by branched and self-supporting canes, conical fruit that is longer than broad, an early primocane season production period, a long production season and light red colored fruit with uniform drupelets.

4 Drawing Sheets

STATEMENT REGARDING FEDERALLY SPONSORED RESEARCH OR DEVELOPMENT

The disclosed invention was made with government support under Contract No. NYG-2016-17-154 from the United States Department of Agriculture Hatch Funds. The government has certain rights in this invention.

Latin name of the genus and species of the plant claimed: *Rubus idaeus* L.

Variety denomination: 'Crimson Beauty'.

BACKGROUND OF THE INVENTION

The present invention relates to a new and distinct primocane bearing (fall bearing) red raspberry plant designated as 'Crimson Beauty'. The plant is botanically known as *Rubus idaeas* L. The new and distinct red raspberry originated from a hand-pollinated cross of the Cornell selection 'NY14-87' (unpatented) and Cornell selection 'NY13-80' (unpatented). This cross was made and the resulting seedling, grown in Geneva, New York. The seedling was grown in a pot in soilless substrate under high tunnels and selected in 2017 and was designated 'NY17-25' for testing. The new plant has been asexually propagated by dormant canes since 2018 and was established in tissue culture for propagation of plants for further trials in late 2018 in Geneva, New York. This propagation has demonstrated that the combination of traits that characterize this plant are fixed and remain true to type through successive generations of asexual propagation.

SUMMARY OF INVENTION

'Crimson Beauty' is primarily adapted to the climate and growing conditions of west central New York and other regions of similar temperate climate. This climate allows for the development of moderate height primocanes that produce flowers in early summer and mature fruit in the early fall season starting in late July extending to early September. 'Crimson Beauty' benefits from the use of protective structures such as plastic hoop houses or high tunnels, which allow for optimal cane growth and weather protection during high temperatures and summer rains. When allowed to produce a floricane crop in the following summer, this portion of the crop is a smaller percentage of the total yield with similar mean fruit weight and lesser maximum fruit weight.

'Crimson Beauty' has a winter hardiness on floricanes for surviving in USDA Plant Hardiness Zone 5b, and a winter hardiness on underground crown for surviving in USDA Plant Hardiness Zone 4b. 'Crimson Beauty' drought tolerance is moderate. Recommended irrigation equivalent of 1 acre inch per week during the vegetative stage and 2 acre inches per week during fruit development through harvest.

The following traits have been repeatedly observed and are determined to be unique characteristics of 'Crimson Beauty', which in combination distinguish this raspberry plant as a new and distinct plant:

1. Early harvest season on primocanes;
2. Primocane crops on approximately 50% of the cane;
3. Extended fall fruiting season;
4. Moderate cane height with significant branching;
5. Bright, glossy, light red, cone shaped fruit with uniform drupelets; and
6. Moderately dense, short prickles on mature sections of the canes.

The new plant differs from its parents by combining the sturdy, upright canes of the seed parent 'NY14-87' (female) and early season primocane fruiting and light red fruit the pollen parent 'NY13-80' (male). 'NY14-87' produces medium sized conic fruit that is medium red and relatively soft that is concentrated in the top ⅓ section of the primocanes. 'NY13-80' is more vigorous and produces a smaller, light red, cone shaped fruit on tall, somewhat spindly canes. The new plant is dissimilar to other primocane fruiting varieties currently grown in New York in that the new plant has a very early primocane harvest season, produces glossy, light red fruit, and has sturdy, self-supporting canes with many branches and fruits on 50% of the primocane length. The new plant is most similar in fruiting season and cane stature to the patented plant 'Crimson Treasure' (U.S. Plant Pat. No. 32,799P2) which has sturdy upright primocanes with many branches and sparse prickles. The fruiting season of the new plant begins somewhat earlier than 'Crimson Treasure' which is earlier than other commercial varieties. This is facilitated by the medium height canes that develop flowers in late June, earlier than other varieties. The canes of 'Crimson Beauty' are typically lightly blushed red-purple (red-purple group 60B) over light yellow-green color (yellow-green group 147A) when mature with moderately dense, red-purple (red-purple group 61B) colored prickles on the mature sections. The fruit of the new plant are most similar in shape to the fruit of the primocane variety 'Crimson Treasure' which has large, red fruit that tend to be dull in surface color and are less distinctly conical in shape. In contrast, the fruit of the new plant are longer than the fruit of 'Crimson Treasure' and more conic in shape, are more glossy at full maturity. It is similar in cane structure to the variety 'Caroline' (U.S. Plant Pat. No. 10,412) which has variably pigmented red purple to greyed yellow canes, with few short prickles and a waxy coating. In comparison to the similar varieties 'Caroline' and 'Crimson Treasure', 'Crimson Beauty' differs by the following combination of characteristics described in Table 1 and Table 2. Color terminology is based on The Royal Horticultural Society Colour Chart (2001 edition).

TABLE 1

Plant and Fruit Characteristics

| Characteristic | 'Crimson Beauty' | 'Caroline' (U.S. Plant Pat. No. 10,412) | 'Crimson Treasure' (U.S. Plant Pat. No. 32,799 P2) |
|---|---|---|---|
| 1. Mature primocane color | Red-purple 60B blush over Yellow-green 147A | Red purple 59B blush over Greyed-yellow 160A | Yellow-green 144B |
| 2. Fruit shape | Conical | Broad conical | Conical |
| 3. Fruit length (mm) | 24 | 18 | 23 |
| 4. Fruit width (mm) | 20 | 19 | 20 |
| 5. Fruit length × width ratio | 1.2 | 0.9 | 1.1 |
| 6. Mean fruit weight-primocane | 4.2 g | 2.5 g | 3.1 g |
| 7. Maximum fruit weight-primocane | 6.8 g | 3.8 g | 6.4 g |
| 9. Mean fruit weight-floricane | 5.0 g | 2.2 g | 2.9 g |
| 8. Maximum fruit weight-floricane | 5.9 g | 3.5 g | 5.8 g |
| 9. Mature fruit color | Red 45A | Red 45A | Red 45A |

TABLE 1-continued

Plant and Fruit Characteristics

| Characteristic | 'Crimson Beauty' | 'Caroline' (U.S. Plant Pat. No. 10,412) | 'Crimson Treasure' (U.S. Plant Pat. No. 32,799 P2) |
|---|---|---|---|
| 10. Canes per plant | 17 | 31 | 24 |
| 11. Fruiting laterals per primocane | 15 | 14 | 18 |
| 11. Leaflet number | Primarily 5, often lobed or fused primary and secondary leaflets | 5 | Primarily 5, sometimes 3 or mixed |

BRIEF DESCRIPTIONS OF THE PHOTOGRAPHS

The color photographs illustrate typical characteristics of the new plant 'Crimson Beauty' and are as true to color as reasonably possible with photographic reproductions of this type. Color in the photographs may differ slightly from the color value cited in the detailed botanical description, which accurately describes the color of 'Crimson Beauty'. The photographs of canes and fruit were taken in Geneva, New York in the second year of harvesting fruit in the plot.

DETAILED BOTANICAL DESCRIPTION

Figure 1A:
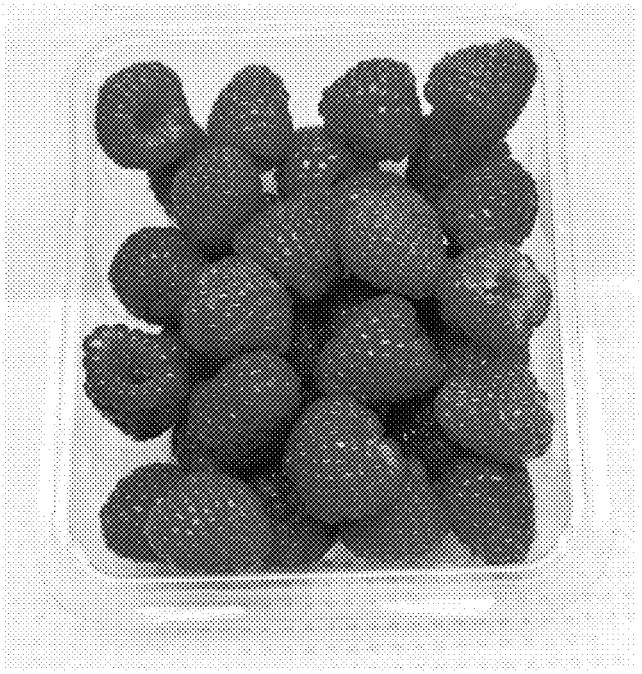
FIG. 1A shows the typical fruit shape and size of 'Crimson Beauty' in a container.
Figure 1B:
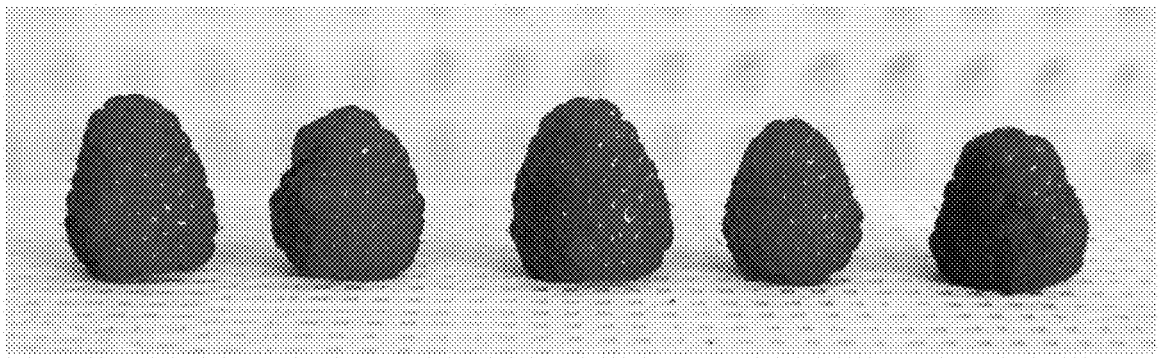
FIG. 1B shows a side view.
Figure 1C:
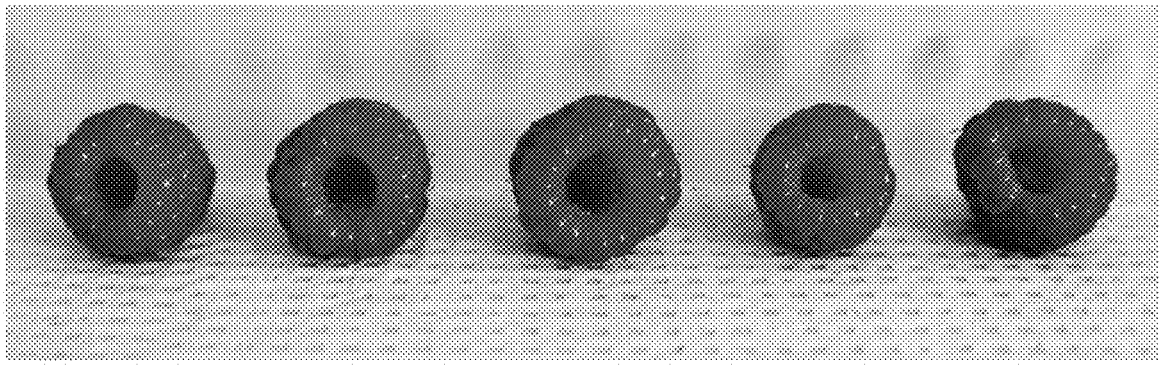
FIG. 1C shows a top view showing the cavity.
Figure 2A:
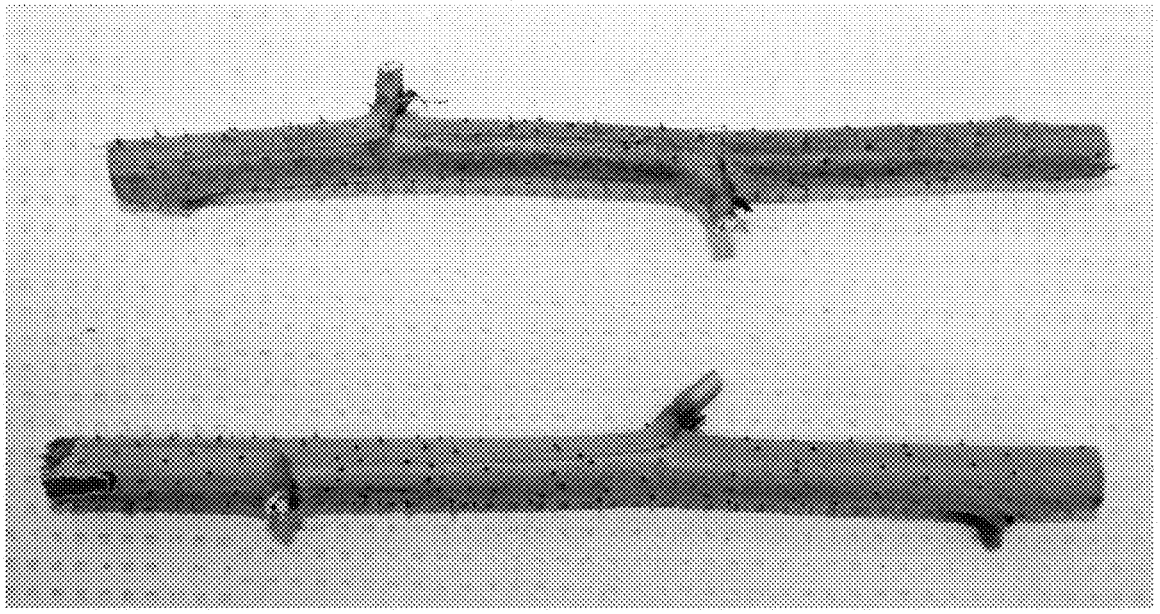
FIG. 2A shows the typical primocane pigmentation and prickle density of mature canes for 'Crimson Beauty'.
Figure 2B:
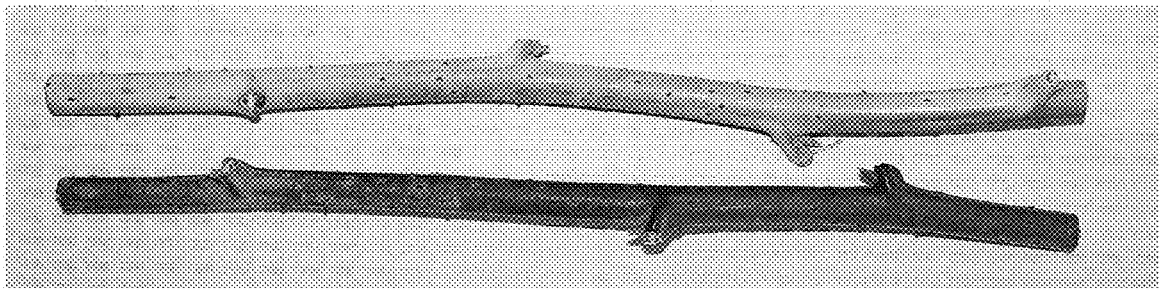
FIG. 2B shows the typical primocane pigmentation and prickle density of mature canes for 'Caroline'.
Figure 2C:
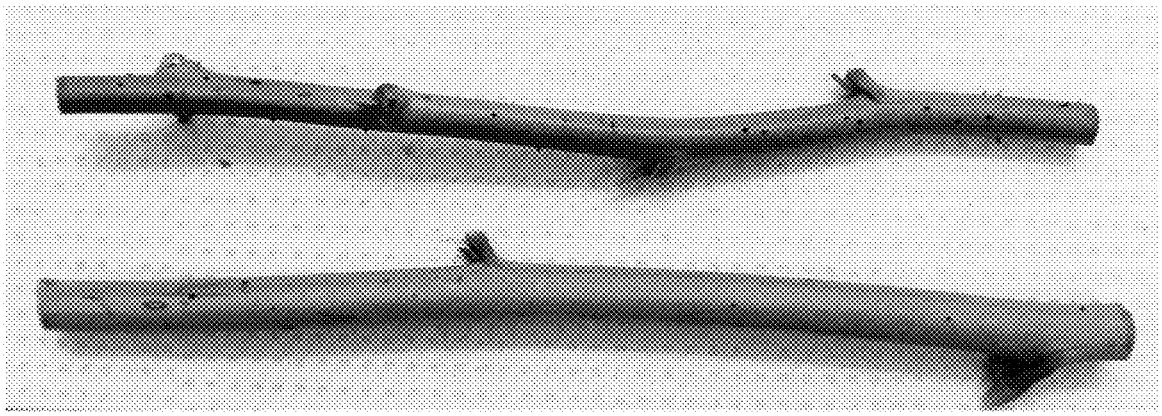
FIG. 2C shows the typical primocane pigmentation and prickle density of mature canes for 'Crimson Treasure'.
Figure 3A:
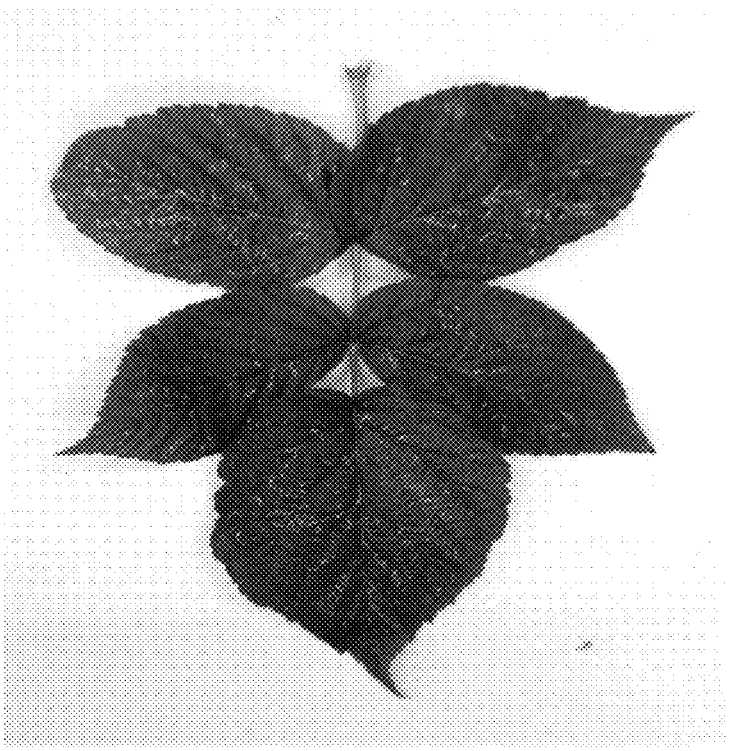
FIG. 3A shows top surface of typical 5 leaflet mature leaflet arrangements found on 'Crimson Beauty'.
Figure 3B:
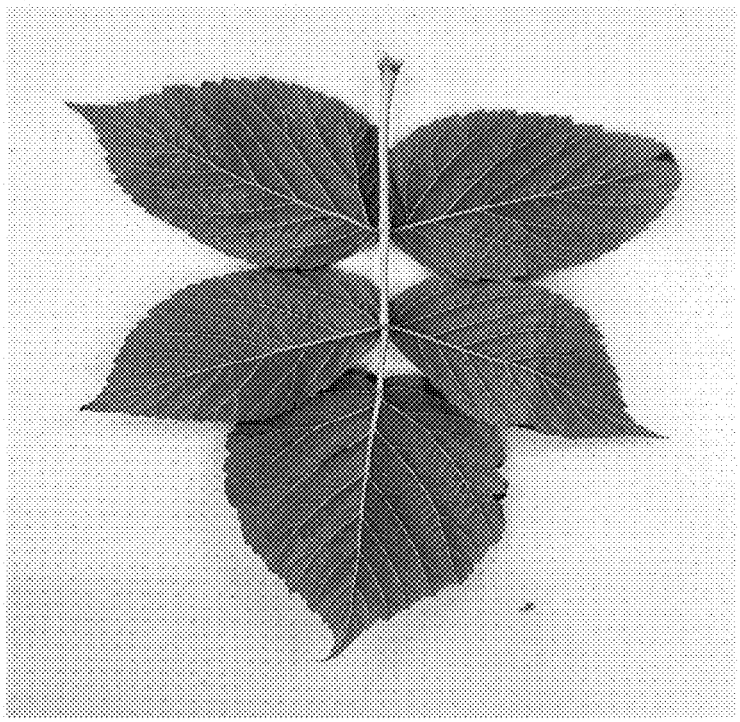
FIG. 3B Bottom surface of typical 5 leaflet mature leaflet arrangements found on 'Crimson Beauty'.
Figure 4:
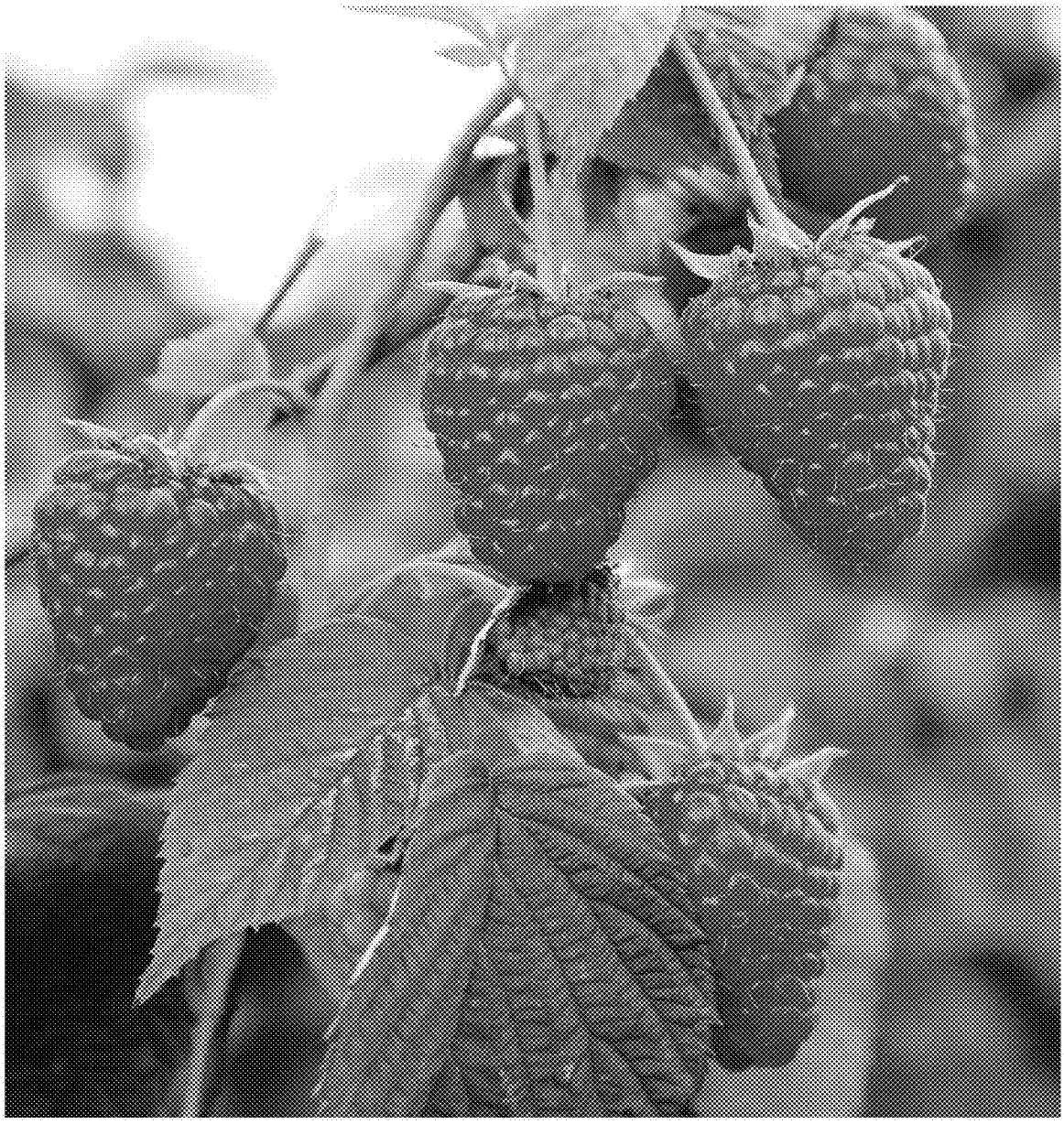
FIG. 4 shows fruiting habit of 'Crimson Beauty' showing presentation of fruit with uniform drupelets. The fruit hangs freely downward and is easily accessible for harvest.

'Crimson Beauty' has not been observed under all possible environmental conditions and as such the characteristics may vary in detail depending on weather conditions, day length, soil type and location.

The photographs together with the description of the new raspberry 'Crimson Beauty' are based upon the observations taken during the 2023-24 growing seasons in Geneva, NY. Measurements were taken on plants grown in the soil in a perennial planting in a high tunnel system that was planted in Geneva, NY in 2022 with the canes emerging naturally in late April each year. Flower measurements and characteristics were taken from primary flowers and fruit measurements from primary and secondary fruit. Mean measurements of fruit size were taken on 10 fruit samples throughout the season. Measurements of flower and fruit parts are means of 10 samples. Cane measurements and prickle density taken within the center third of the cane unless otherwise noted.

Classification:
*Family*.—Rosaceae
*Botanical*.—*Rubus idaeus* L.
*Common name*.—Red Raspberry.
Parentage: 'NY14-87' (Unpatented) x 'NY13-80' (unpatented).
Plant:
*Propagated*.—Asexual dormant canes, tissue culture.
Primocanes:
*Cane color*.—Yellow-green 147A with red-purple 60B blush.
*Prickles*.—Present.
*Cane length*.—1.45-1.71 m; mean 1.55 m.
*Cane diameter*.—8-11 mm; mean 9.9 mm.
*Number of fruiting lateral branches*.—13-21; mean 15.
*Maximum fruiting lateral length*.—79 cm.
*Cane pubescence*.—None.
*Location*.—Geneva, New York.
*Bud burst in spring*.—Approximately March 28.
*Primocane emergence from soil*.—Approximately March 20.
*Bloom on floricanes*.—Approximately May 15, lasting 2-3 weeks.
*Bloom on primocanes*.—Approximately July 1, lasting 8 weeks.
Prickles:
*Density*.—Dense at base, moderate at middle third.
*Form*.—Thin.
*Length*.—Short-2 mm mean.
*Apex*.—Straight downward.
*Color*.—Red-purple 61B on mature canes.
Leaves:
*Type*.—Compound; typically 5 leaflets; approximately 15% secondary leaflet(s) fused with terminal leaflet or fused with other secondary leaflets.
*Mature leaflet color*.—Upper surface Green 137A; lower surface Yellow-green 147B.
*Arrangement*.—Free.
*Terminal leaflet length*.—10.5-12.5 cm; mean 11.2 cm.
*Terminal leaflet width*.—7.8-9.7 cm; mean 8.6 cm.
*Terminal leaflet length to width ratio*.—1.3.
*Center leaflet length*.—8.5-10.1 cm; mean 9.0 cm.
*Center leaflet width*.—4.7-5.8 cm; mean 5.2 cm.
*Center leaflet length to width ratio*.—1.7.
*Basal leaflet length*.—9.9-11.3 cm; mean 10.4 cm.
*Basal leaflet width*.—6.4-7.6 cm; mean 7.8 cm.
*Basal leaflet length to width ratio*.—1.4.
*Leaflet shape*.—Ovate.
*Terminal leaflet tip*.—Acuminate.
*Basal leaflet attachment*.—Cuspidate.
*Leaflet margins*.—Doubly serrate.
*Terminal leaflet number of serrations*.—91 mean.
*Basal leaf attachment*.—Cordate to auriculate.
*Leaflet overlap*.—Common.
*Petiole length*.—5.8 cm.
*Petiole width*.—8.2 mm.
*Petiole prickles*.—Present, sparse.
*Petiole prickle apex*.—Slight downward toward stem.
*Petiole color*.—Yellow-green 147A.
Stipules:
*Quantity per leaf*.—2.
*Shape*.—Straight and erect.
*Length*.—7.5-9.0 mm; mean 7.85 mm.
*Color*.—Yellow-green 147A.
Flowers:
*Diameter*.—2.1-2.5 cm; mean 2.3 cm.
*Bud shape*.—Conical.
*Fragrance*.—None.
*Petals number*.—Typically 5, occasionally 6 in primary flowers.
*Petal shape*.—Obovate.
*Petal length*.—7.0-8.0 mm; mean 7.6 mm.
*Petal width*.—2.0-3.5 mm; mean 2.75 mm.
*Petal length to width ratio*.—2.8.
*Petal color*.—White 155C.
*Sepal number*.—Typically 5; sometimes as many as 8 in primary flowers.
*Sepal length*.—9.5-13.0 mm; mean 11.2 mm.
*Sepal color*.—Upper surface Yellow-green 147A; lower surface Yellow-green 147B.
*Mean stigma number*.—152.
*Stigma color*.—White 155B.
*Mean stamen number*.—105.
*Anther color*.—White 155A.
*Anther filament color*.—White 155D.
*Stamen height*.—Below stigmatic surface.
Fruit:
*Shape*.—Conic.
*Fruit length*.—1.9-2.8 cm; mean 2.4 cm.
*Fruit width*.—1.8-2.2 cm; mean 2.0 cm.
*Fruit length to width ratio*.—1.17.
*Weight*.—Primocane: 3.5-6.6 g; mean 4.2 g.
*Weight*.—Floricane: 3.4-5.9 g; mean 5.0 g.
*Number of drupelets*.—160 for mean primocane fruit size.
*Color of harvest mature fruit*.—Red group 45A.
*Color of fully mature fruit*.—Red group 45C.
*Pedicel diameter*.—1 mm.
*Mean pedicel length*.—35 mm.
*Range*.—21 mm to 51 mm.
*Pedicel color*.—Yellow-green group 147A.
*Pedicel prickles*.—Present; moderate number; curved back towards cane.
*Adherence to receptacle*.—Medium.
Pest and disease reactions:
*Spotted wing drosophila* (*Drosophila suzukii*).—Susceptible.
*Two spotted spider mite* (*Tetranychus urticae*).—Susceptible but uncommon.
*Grey fruit mold* (*Botrytis cinerae*).—Susceptible.
*Powdery mildew* (*Podosphaera aphanis var. aphonic*).—Resistant.
*Yellow rust* (*Phragmidium rubi-idaei*).—Resistant.

I claim:

1. A new and distinct raspberry plant named 'Crimson Beauty', as herein described and illustrated by the characteristics set forth above.

* * * * *